United States Patent [19]
Koenig, Jr. et al.

[11] Patent Number: 5,248,301
[45] Date of Patent: * Sep. 28, 1993

[54] TRANSCUTANEOUS INFUSION APPARATUS AND METHODS OF MANUFACTURE AND USE

[75] Inventors: Marvin E. Koenig, Jr., Roseville; Melvin B. Moschler, Jr., Britt, both of Minn.

[73] Assignee: Medfusion, Inc., Hilliard, Ohio

[*] Notice: The portion of the term of this patent subsequent to Aug. 4, 2009 has been disclaimed.

[21] Appl. No.: 441,299

[22] Filed: Nov. 27, 1989

Related U.S. Application Data

[63] Continuation-in-part of Ser. No. 157,517, Feb. 2, 1988, abandoned, which is a continuation-in-part of Ser. No. 128,046, Dec. 3, 1987, abandoned.

[51] Int. Cl.$^5$ .............................................. A61M 5/00
[52] U.S. Cl. ................................. 604/164; 604/165; 604/175; 604/263
[58] Field of Search ................. 604/93, 117, 164, 165, 604/166–167, 169, 170, 175, 272, 110, 263

[56] References Cited

U.S. PATENT DOCUMENTS

| | | |
|---|---|---|
| 2,751,653 | 10/1951 | Bastien . |
| 3,030,953 | 4/1962 | Koehn .................................. 604/166 |
| 3,063,451 | 11/1962 | Kowalk . |
| 3,566,874 | 3/1971 | Shepherd . |
| 3,598,127 | 8/1971 | Wepsic . |
| 3,788,320 | 1/1974 | Dye ...................................... 604/272 |
| 3,792,703 | 2/1974 | Moorehead . |
| 3,875,938 | 4/1975 | Mellor . |
| 3,994,287 | 11/1976 | Turp et al. ........................... 604/167 |
| 3,995,623 | 12/1976 | Blake et al. . |
| 4,013,080 | 3/1977 | Froning . |
| 4,072,146 | 2/1978 | Howes . |
| 4,257,416 | 3/1981 | Prager . |
| 4,364,383 | 12/1982 | Vcelka . |
| 4,377,165 | 3/1983 | Luther et al. . |
| 4,406,656 | 9/1983 | Hattler et al. . |
| 4,540,411 | 9/1985 | Bodicky . |
| 4,565,545 | 1/1986 | Suzuki ................................. 604/272 |
| 4,569,675 | 2/1986 | Prosl et al. . |
| 4,573,981 | 3/1986 | McFarlane . |
| 4,643,199 | 2/1987 | Jennings, Jr. et al. . |
| 4,655,751 | 4/1987 | Harbaugh . |
| 4,668,221 | 5/1987 | Luther . |
| 4,673,394 | 6/1987 | Fenton, Jr. et al. . |
| 4,676,783 | 6/1987 | Jagger et al. . |
| 4,702,738 | 10/1987 | Spencer . |
| 4,702,739 | 10/1987 | Milorad . |
| 4,721,506 | 1/1988 | Teves . |
| 4,725,267 | 2/1988 | Vailancourt . |
| 4,747,831 | 5/1988 | Kulli . |
| 4,762,516 | 8/1988 | Luther et al. . |
| 4,846,805 | 7/1989 | Sitar . |
| 4,850,961 | 7/1989 | Wanderer et al. .................. 604/164 |
| 5,135,502 | 8/1992 | Koenig, Jr. et al. ............... 604/164 |

FOREIGN PATENT DOCUMENTS

| | | |
|---|---|---|
| 000841 | 5/1980 | European Pat. Off. . |
| 1131865 | 10/1967 | United Kingdom . |
| 8803035 | 5/1988 | World Int. Prop. O. . |

*Primary Examiner*—Ralph Lewis
*Attorney, Agent, or Firm*—Wood, Herron & Evans

[57] ABSTRACT

Apparatus for accessing the circulatory system of a person or animal includes a port and a device for accessing the port. The access device has a solid introducer with a catheter received thereabout. The introducer and catheter are covered by telescoping containers which expose the insertion ends of the introducer and catheter only at the time of insertion. The catheter is separable from the access device after insertion.

33 Claims, 12 Drawing Sheets

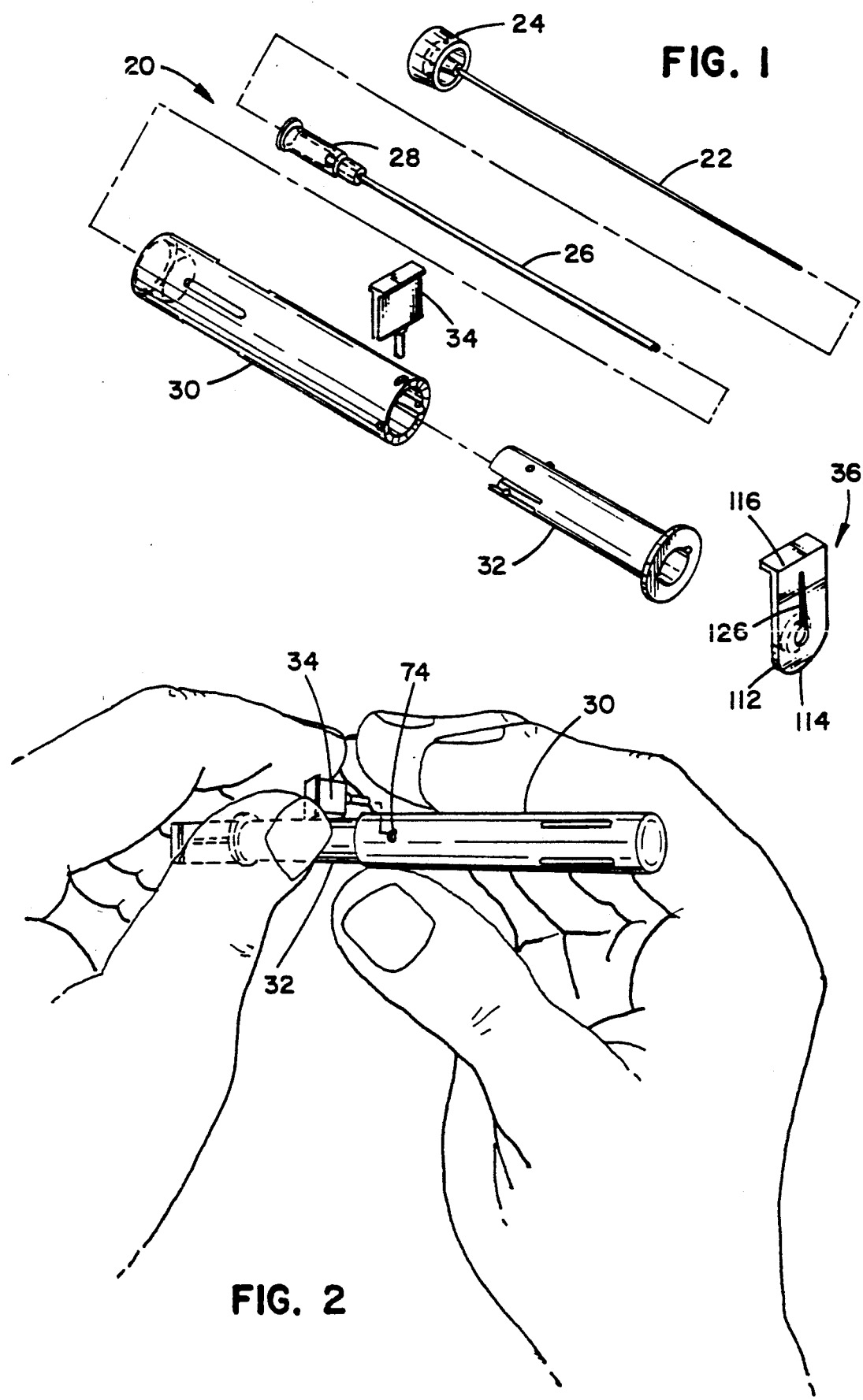

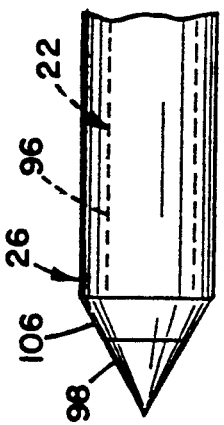
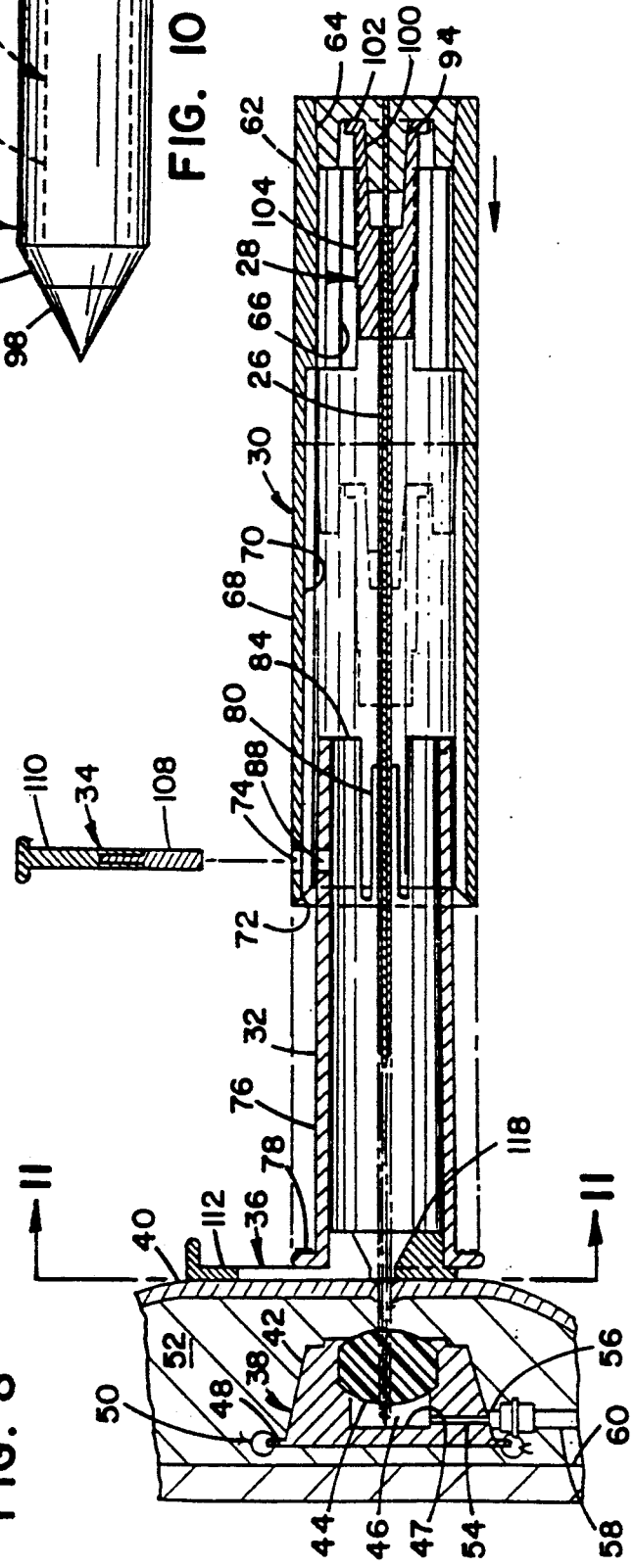
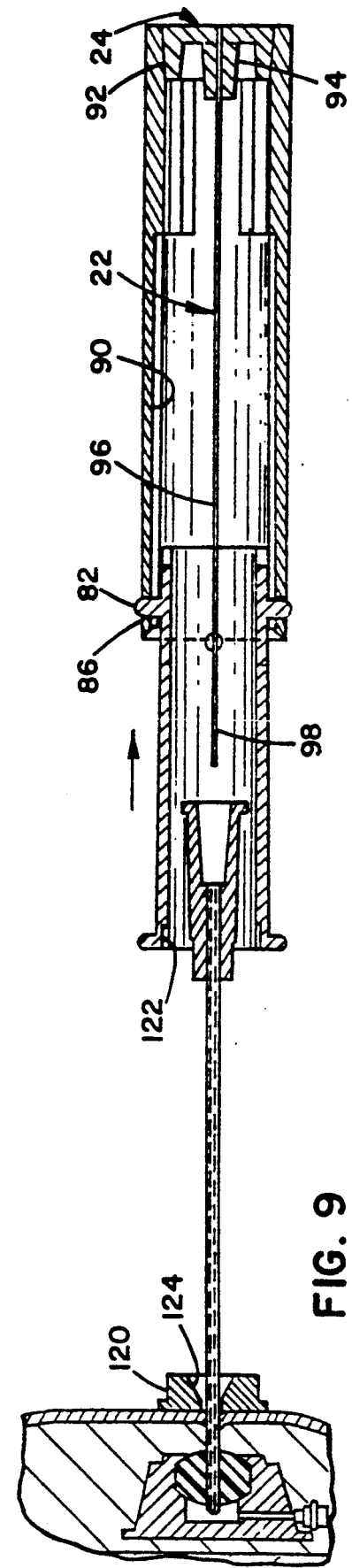

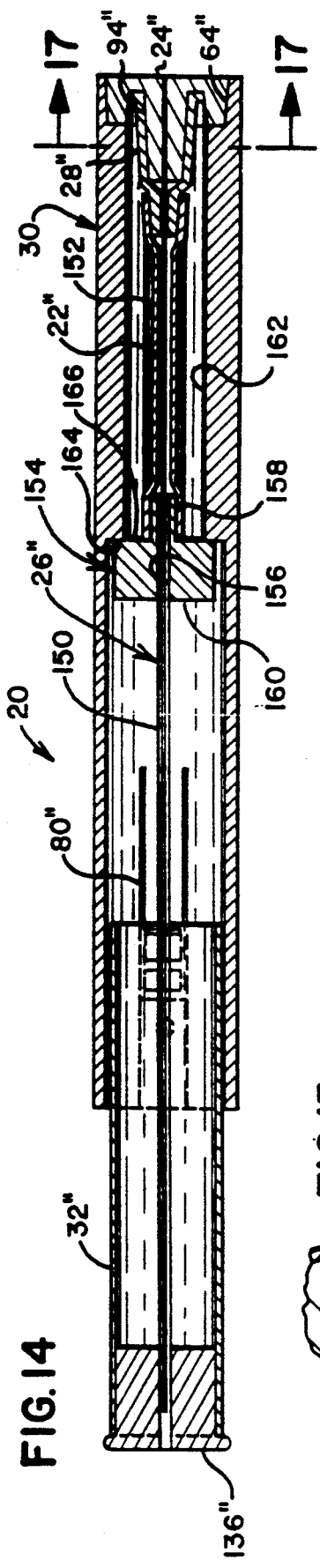
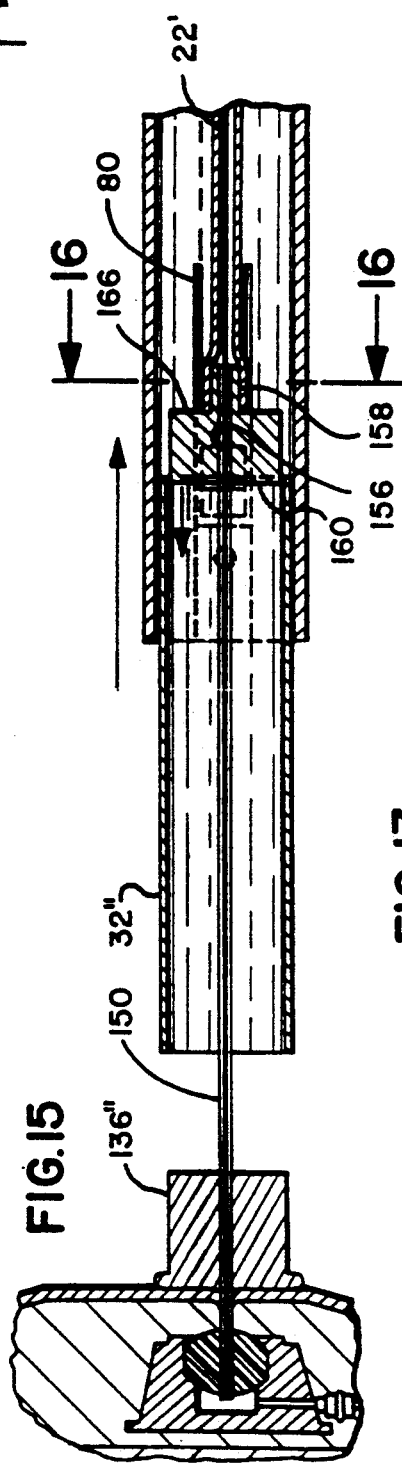
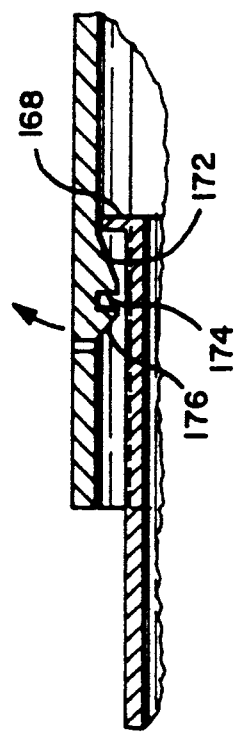
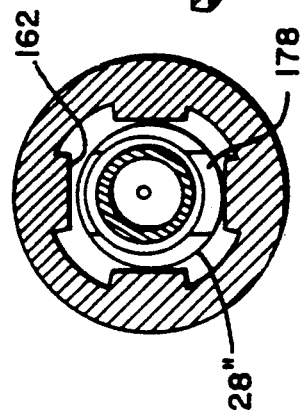
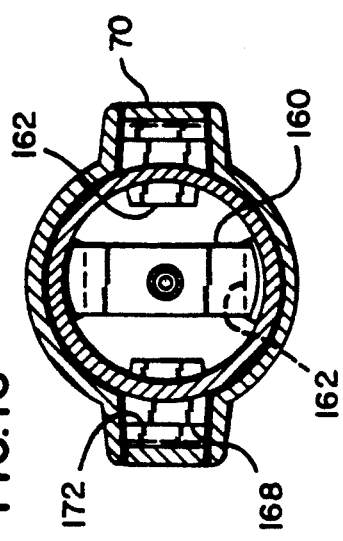

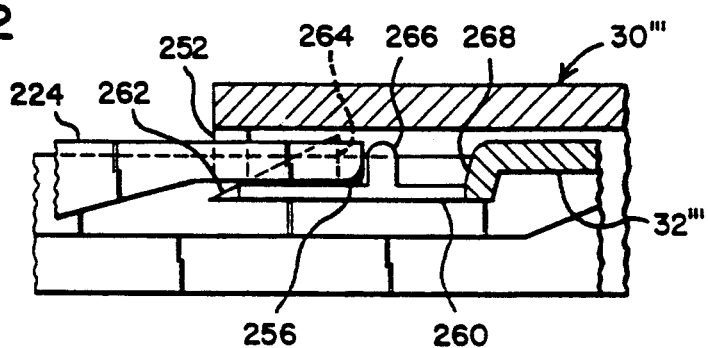
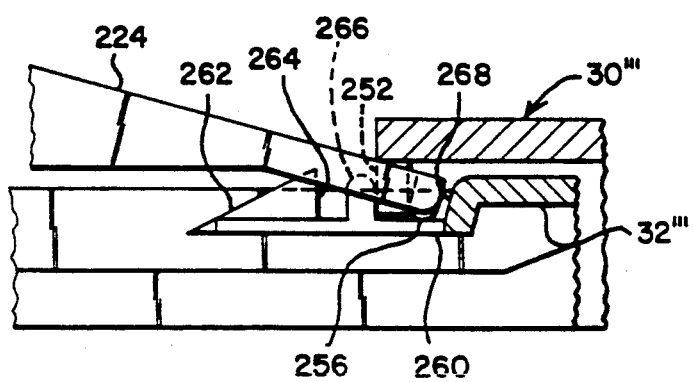
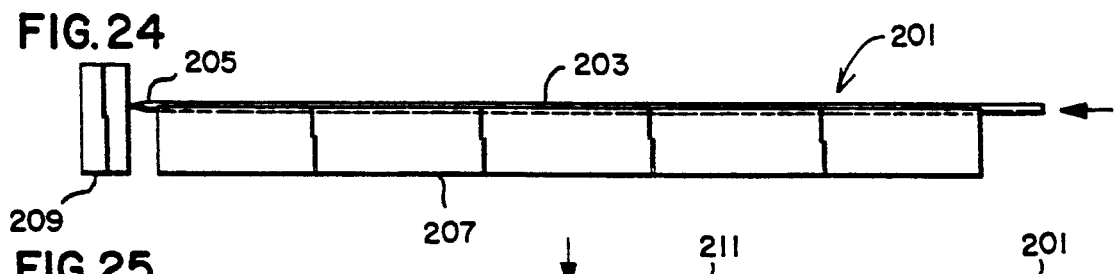
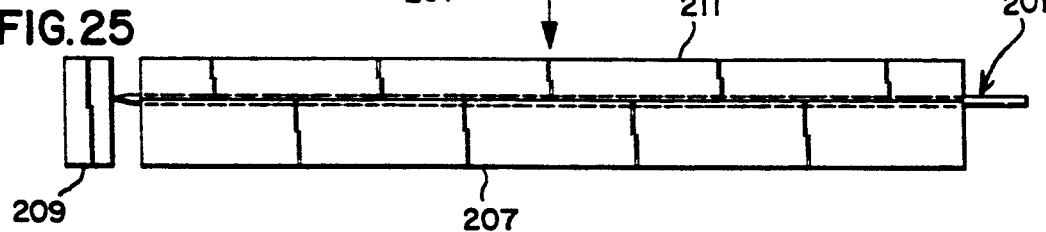
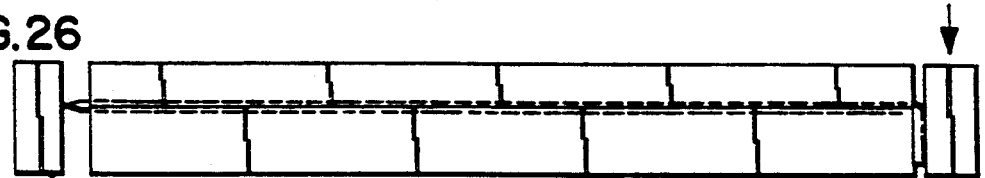
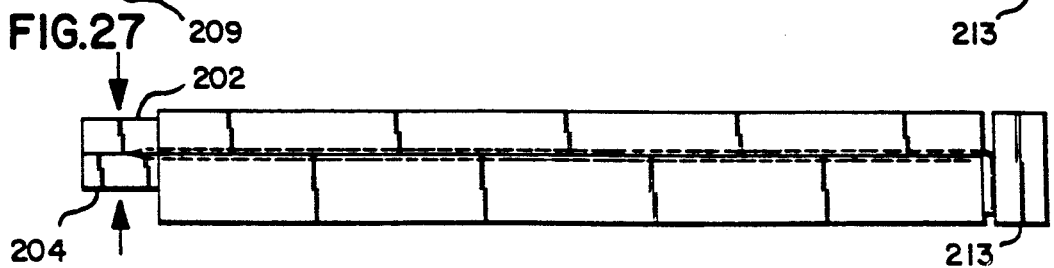

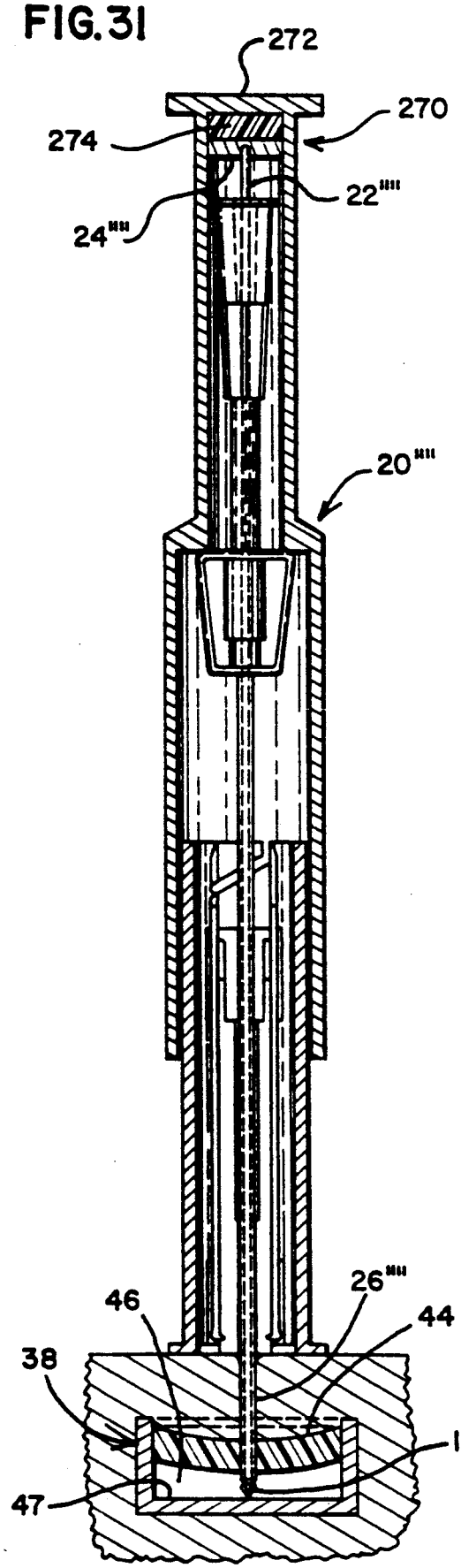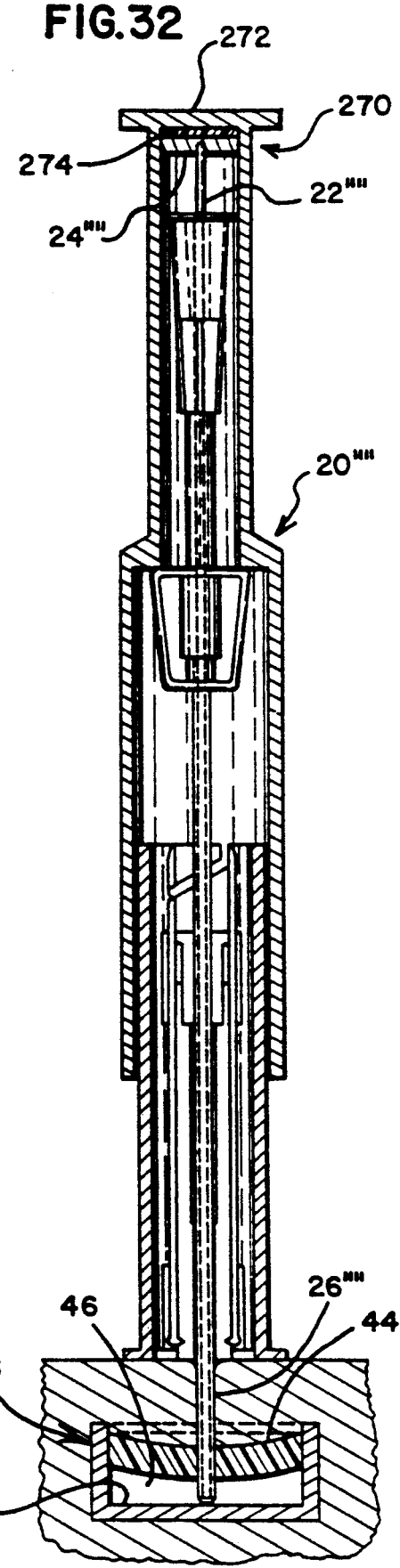

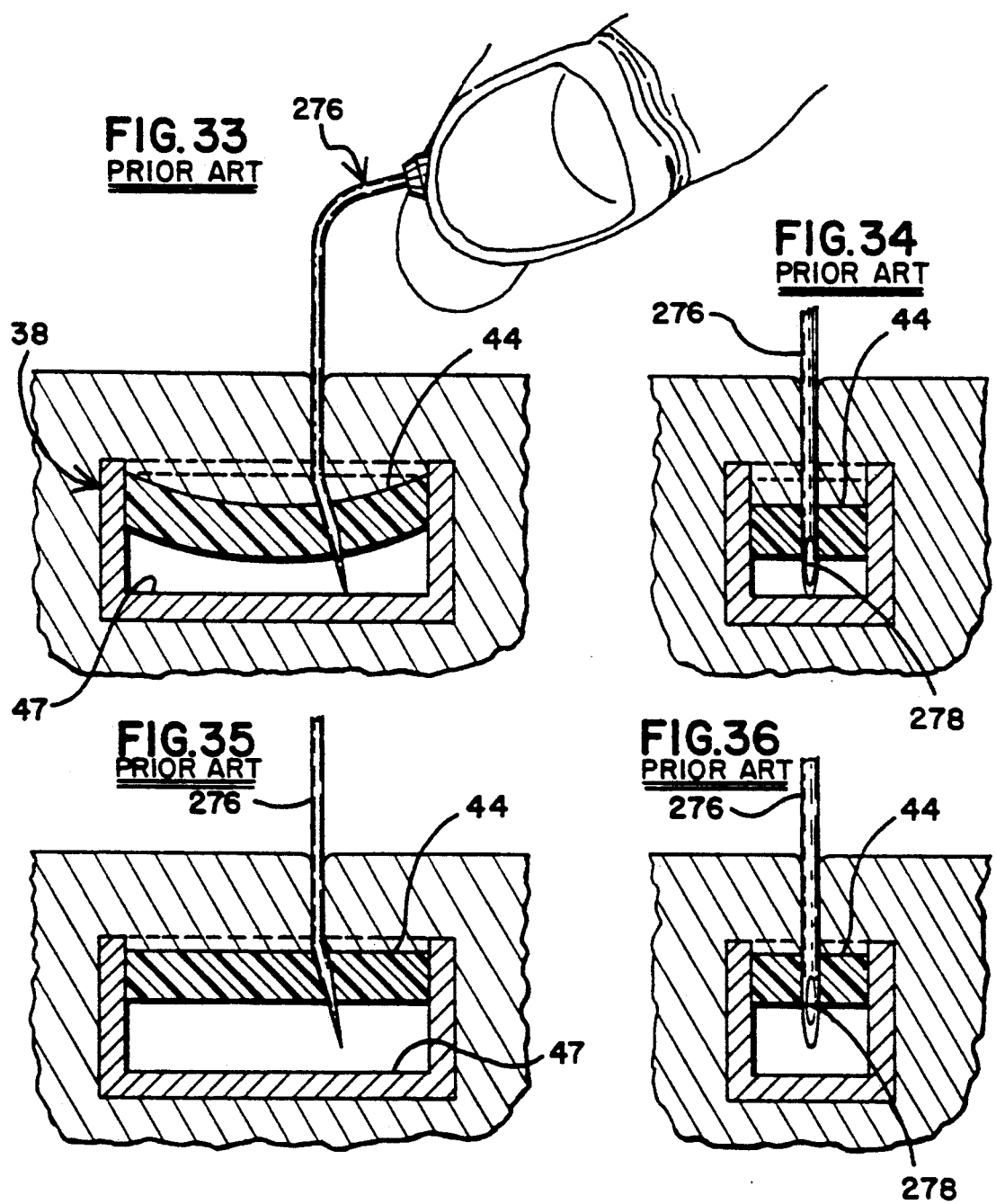

TRANSCUTANEOUS INFUSION APPARATUS AND METHODS OF MANUFACTURE AND USE

This application is a continuation-in-part of application Ser. No. 07/157,517, filed Feb. 2, 1988,(now abandoned), which is a continuation-in-part of application Ser. No. 07/128,046, filed Dec. 3, 1987, (now abandoned).

FIELD OF THE INVENTION

The present invention is directed generally to medical devices and, more particularly, to devices for accessing an infusion site of a person or animal. The present device includes a solid introducer needle with surrounding catheter for accessing a surgically implanted port which is in fluid communication usually with a blood vessel.

BACKGROUND OF THE INVENTION

Introduction of fluids into a patient using a catheter and insertion device is known. For intravenous infusion, the most common insertion device is a syringe with a hollow needle received in a catheter. After insertion, some blood is extracted into the syringe before the syringe is removed from the catheter and a Luer coupler on the free end of the catheter connected to a fluid delivery system. These devices do not commonly have pre or post insertion needle covers or protectors.

Another known system for intravenous infusion has a flexible catheter disposed within the bore of a hollow needle. After the needle is inserted into a vein, the catheter is pushed through the hollow end of the needle as the needle is retracted. A significant drawback of this type of device is that once the insertion needle is withdrawn, the needle cannot be removed from the catheter. The Luer lock or other coupling mechanism has a diameter too large to pass through the needle bore. Since the needle cannot be removed, it is continuously present on the catheter outside the patient's body and is a continuous source of possible problems.

A separable catheter insertion device is shown in U.S. Pat. No. 3,682,173. A longitudinal slot runs the length of the needle and of the hub member secured to the needle. The slot facilitates removal of the catheter from the needle after insertion of the catheter into the patient.

In a related application filed Oct. 31, 1986, having Ser. No. 925,313 and assigned to the Assignee of the present application, a splittable needle functions to emplace a catheter. Once the catheter is in place, the applicator operates to slit the needle so that it can be removed from the catheter and disposed of.

The indicated devices with hollow needles allow for the extraction or flashback of blood when the vein has been pierced. In many cases such feature is important. There is another class of cases, however, where it is not necessary. Particularly, flashback does not occur when a catheter is inserted into a previously surgically implanted port. A port is a device which forms a reservoir with a rubberized septum on the access side nearest the skin and a solid surface on a side opposite. The port further includes a tube leading from the reservoir to an infusion site such as a vein or other blood vessel. The device is placed under the skin to provide a bacterial covering and is placed in a location convenient to the doctor considering the intended use. A port is commonly used to administer chemotherapy, is used to advantage in areas where the veins of the patient have collapsed or collapse easily, and may be used specifically to avoid flashback and provide safety to a clinician when treating a patient, for example, with AIDS.

The syringe type and other devices mentioned above which are known and used for intravenous access are not generally appropriate for accessing a port. The catheters do not have sufficient radial strength to avoid collapse at the septum and the internal diameter of the catheter is small and limited by the size needle possible considering the use.

The infusion system disclosed in U.S. Pat. No. 4,569,675 describes very briefly a needle device for introducing a catheter to a port wherein the needle could be solid and fits within the catheter. The device, however, is very simple and does not show radial stabilization or needle container coverage before and after insertion or any of the other features and advantages of the present invention.

A very frequently used known device for accessing ports is simply a hollow needle (no catheter). One problem with a hollow needle is the coring of the septum produced by the tip of the needle. Because of the causticity of medicines directed into a port and thereafter the venous system, it is important that medicines not leak from the port. Any coring of the septum reduces substantially the number of times which the septum can be accessed without unacceptably increasing the risk of leakage. Furthermore, the fact of coring limits the cross-sectional size of needles which can be introduced to a port. To avoid coring, needle tips are often given wedge type shapes or boat-like type shapes. Such needle tips, however, then often leads to another problem wherein they do not provide an unobstructed opening to the port reservoir (see FIGS. 33-36).

Thus, to summarize, many known catheter insertion devices enclose a relatively flexible catheter and are primarily intended for directly accessing a bio-target, commonly a vein. Other port access devices are hollow needles and do not emplace catheters. Coring can be a problem. With the insertional devices enclosing catheters, the catheters are necessarily small and lack compressive strength. The present invention uses a solid introducer and a catheter thereover and includes a containing type holder with radial stabilization for the needle and catheter so that it is particularly suited for accessing a port.

SUMMARY OF THE INVENTION

The present transcutaneous infusion apparatus includes a port, a needle, catheter mechanism, and mechanism for holding the needle and the catheter mechanism in order to insert them through the septum and into the reservoir of the port. The catheter mechanism has a part which fits about a portion of the shaft of the needle while allowing the tip of the needle to be exposed. The holding mechanism includes mechanism for pushing the needle and the catheter mechanism during insertion until the needle contacts the solid surface opposite the septum of the port. The pushing mechanism includes mechanism for yielding with respect to the needle to allow the catheter mechanism to more closely approach the solid surface. The needle and the holding mechanism are separable from the inserted catheter mechanism so that they may be discarded while leaving the catheter mechanism in place.

In another embodiment, the holding mechanism includes a pair of arms having mating grooves to receive and support the catheter mechanism and needle thereby stabilizing them as they are inserted through the skin of the patient and the septum of the port. In a further embodiment, the tip of the needle is coined to have a knife-like edge in order to cut the skin thereby reducing the force necessary to insert the needle and catheter through the skin.

The present invention is also directed to a method of using the access device which includes the steps of inserting the solid introducer while surrounded by the catheter through the skin of the person or animal and the septum of the port, and then retracting and removing the introducer from the catheter and covering it to prevent any accidental stick.

In further embodiments of the method, telescoping containers are locked with respect to one another before the distal ends of the introducer and catheter are exposed so that they may be inserted. In still further embodiments of the method, the introducer is axially covered by the containers as the introducer is retracted and removed from the catheter so that when the introducer is fully retracted, the telescoping containers are locked with respect to one another leaving the introducer covered.

The present invention is still further directed to a method for making the access device which includes the steps of coining a knife-like edge on the tip of a solid rod to form the introducer or needle, attaching the needle to a hub, sliding catheter mechanism onto the needle, and fitting holding mechanism for the needle and the catheter mechanism to the hub so that the holding mechanism has three positions including a first position wherein the holding mechanism longitudinally covers the needle and catheter mechanism, a second position wherein the ends of the needle and catheter mechanism are exposed for insertion, and a third position wherein the needle is longitudinally covered by the holding mechanism as the holding mechanism and needle are separated from the catheter mechanism.

The access apparatus of the present invention is particularly advantageous since the introducing element is solid and the catheter surrounds it so that on insertion, there is no coring of the septum. In this way, larger catheters may be inserted. Furthermore, the lifetime of a port is substantially increased for a given introducer size. Because ports are surgically implanted, the number of insertions for any one emplaced port or the lifetime is a critical performance parameter.

The present device is of further advantage in that a covering container mechanism is provided which not only longitudinally covers the introducer and catheter before insertion, but also covers the introducer as it is retracted from the catheter after insertion and locks the covering mechanism in place to prevent any accidental pricking prior to responsible discarding.

The present invention is of still further advantage in that one of the catheter embodiments includes a first tube of a TEFLON material (hereinafter either polytetrafluoroethylene or PTFE) which is relatively rigid and a second tube of polyvinylchloride (PVC) or other more flexible material with a connector therebetween. A Luer lock or other suitable coupler is attached to the other end of the second tube. In any case, during insertion the container mechanism pushes on both the needle and the connector so that force is applied to both the needle and the first tube of the catheter thereby preventing the septum from sliding the catheter along the needle rather than allowing the catheter to be inserted along with the needle. The catheter is of further advantage in that the second tube is flexible and, consequently, available for clamping. Furthermore, the flexible second tube is on the opposite side of the connector, i.e., the location at which force is being applied, so that the flexible tube does not collapse during insertion.

The present invention thusly summarized and advantages indicated may, however, be better understood by reference to the drawings briefly described hereinafter and to the detailed description of the preferred embodiment following thereafter.

BRIEF DESCRIPTION OF THE DRAWINGS

FIG. 1 is an exploded perspective view of an access apparatus in accordance with the present invention;

FIG. 2 is a perspective view of the locking pin being removed from aligned openings in the guard and handle;

FIG. 8 is a longitudinal, cross-sectional view of the access apparatus showing in solid lines the apparatus just after removal of the locking pin and showing in broken lines the apparatus after insertion of the introducer and catheter through the septum;

FIG. 9 is a longitudinal, cross-sectional view rotated 90° with respect to the view of FIG. 8 showing the device after retraction of the introducer from the inserted catheter;

FIG. 10 is an enlarged side view of the distal end of the introducer and surrounding catheter;

FIG. 14 is a cross-sectional view of an alternate embodiment;

FIG. 15 is a cross-sectional view of a catheter after insertion relative to the guard and handle in post-insertion position;

FIG. 16 is a cross-sectional view taken along line 16—16 of FIG. 15;

FIG. 17 is a cross-sectional view taken along line 17—17 of FIG. 14;

FIG. 18 is a cross-sectional view of the post insertion lock mechanism;

FIG. 22 is an enlarged, cross-sectional view of an alternate embodiment of the needle and catheter stabilizing legs in a pre-retraction configuration;

FIG. 23 is a view similar to FIG. 22, but shows the retraction configuration;

FIGS. 24–27 illustrate a method for making a needle with a coined tip in accordance with the present invention;

FIGS. 31 and 32 are cross-sectional views of still a further alternate embodiment of an access device in accordance with the present invention showing a yieldable pushing mechanism for the needle; and FIGS. 33–36 are cross-sectional views illustrating the structure and use of a prior art needle relative to a port.

DETAILED DESCRIPTION OF THE PREFERRED EMBODIMENT

Figure 3:
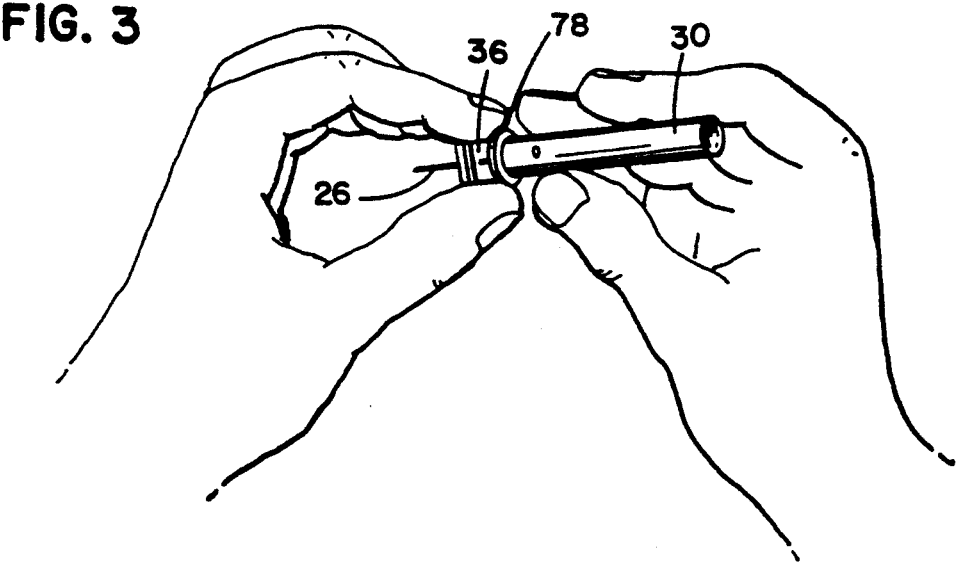
FIG. 3 is a perspective view of the guard being telescoped into the handle to expose the distal ends of the introducer and catheter.
Figure 4:
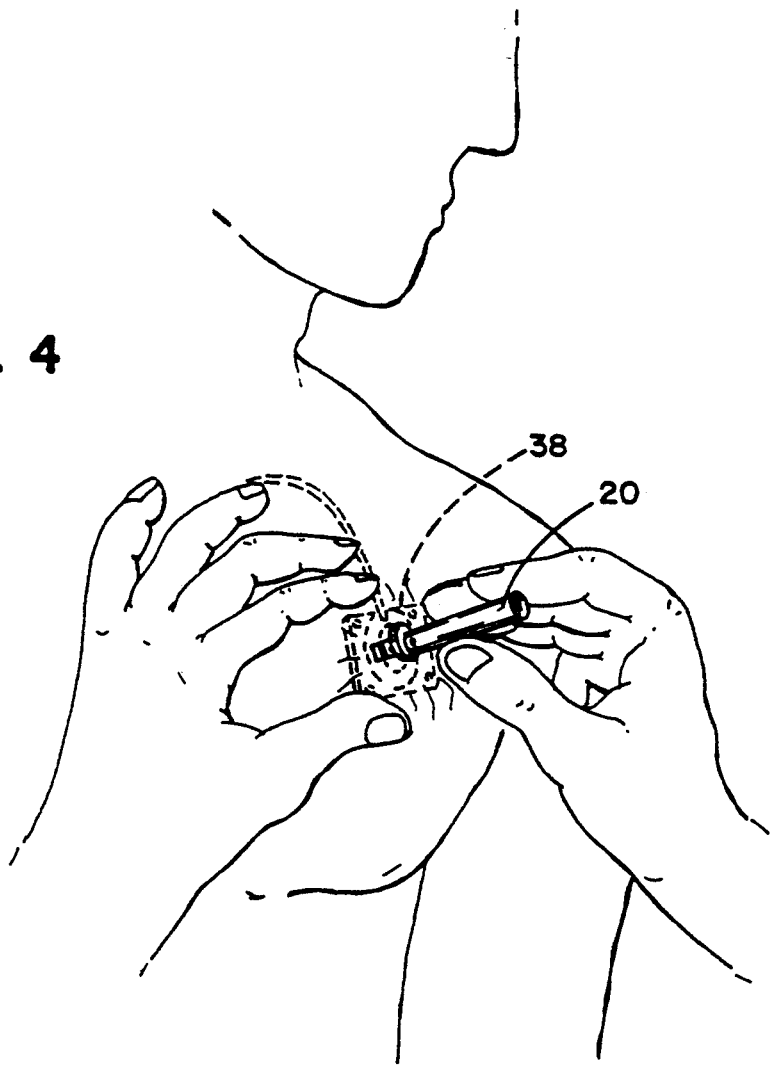
FIG. 4 is a perspective view showing insertion of the introducer and catheter into a port emplaced in the chest of a person.

Referring now to the drawings wherein like reference numerals designate identical or corresponding parts throughout the several views, and referring more particularly to FIG. 1, an access device in accordance with the present invention is designated generally by the numeral 20. Device 20 includes an introducer 22 with a hub 24. The introducer is essentially a needle sized to slidably, but snugly, fit within semi-rigid catheter 26 having a coupler 28, usually a Luer lock, at one end. Hub 24 is held securely at the proximal end of a first container called the handle 30. A second container, called the guard 32, telescopes into and out of handle 30. A locking pin 34 holds the handle 30 and guard 32 in a fixed relationship relative to one another during the pre-insertion. A clamp 36 for catheter 26 is held to the end of guard 32 during pre-insertion.

With reference to FIGS. 8 and 9, a port 38 is shown after surgical emplacement beneath the skin 40 of a body 42 to include a cavity which when covered with a rubberized septum 44 encloses a reservoir 46. Body 42 is made of biocompatible and drug compatible material like titanium or a plastic polymer. Port 38 is oriented with septum 44 on an access side nearest the skin 40. Body 42 then provides a solid surface 47 on a side opposite septum 44. Body 42 has a flange 48 with a plurality of openings through which sutures 50 may be passed to tie port 38 to muscle or other tissue 52. Body 42 further includes a passage 54 exiting reservoir 46 to a fitting 56 to which a tube 58 is fastened. Tube 58 is directed in a fashion not shown into a vein 60 or other infusion site.

Handle 30 is preferably cylindrical and hollow. The proximal end portion 62 is formed to have a frustoconical bore 64. A plurality of ribs 66 extend inwardly from the sidewall 68 of handle 30 at a location adjacent to bore 64. The taper of bore 64 and ribs 66 helps to function to secure hub 24 of needle 22 as discussed further hereinafter. The remaining portion 70 of handle 30 is cylindrically hollow. The distal end 72 has an inwardly directed taper which aids in the assembly of guard 32 to handle 30. An opening 74 is formed in sidewall 68 near the distal end of handle 30 to receive locking pin 34.

Guard 32 preferably has a cylindrical sidewall 76. A flange 78 is formed at the distal end. A pair of cantilevering arms 80 are formed in the proximal end portion of sidewall 76. Each arm 80 includes a protrusion 82 which extends outwardly with respect to sidewall 76. Preferably, arms 80 do not extend completely to proximal end 84. It is noted that protrusion 82 extends outwardly sufficiently far to protrude through openings 86 in the distal end portion of handle 30.

Guard 32 also has an opening 88 in sidewall 76 so that when openings 74 and 88 of cover 30 and guard 32, respectively, are aligned, locking pin 34 can be inserted thereby holding the two containers in a first position which is then fixed relative to the other elements of device 20.

As shown in FIG. 9, handle 30 includes a pair of grooves 90 extending from openings 86 to ridges 66. Protrusions 82 are offset from opening 88 so that grooves 90 receive protrusions 82 when the containers are locked in the first position. When guard 32 is telescoped into handle 30 until proximal end 84 contacts ridges 66 or until flange 78 contacts the distal end of handle 30, protrusions 82 follow grooves 90 and guide the movement of the containers relative to one another. The containers are shown by the broken lines in FIG. 8 in a second position whereby guard 32 is fully telescoped into cover 30.

When guard 32 is telescoped out of cover 30, protrusions 82 again follow grooves 90. In this case, there is no locking pin or any other obstruction to stop guard 32 until arms 80 spring protrusions 82 into openings 86 to define a third position of the containers relative to one another.

Introducer 22 and catheter 26 have proximal and distal end portions with central portions therebetween. Hub 24 axially receives introducer 22 at the proximal end portion of introducer 22. Hub 24 and introducer 22 are fastened together with a medically approved adhesive or another known fashion. Hub 24 has an outer frusto-conical flange 92 which mates with bore 64 and has sufficient longitudinal length to extend approximately between ribs 64 and the proximal end of handle 30. Hub 24 also includes a central boss 94 which receives introducer 22.

Figure 28:
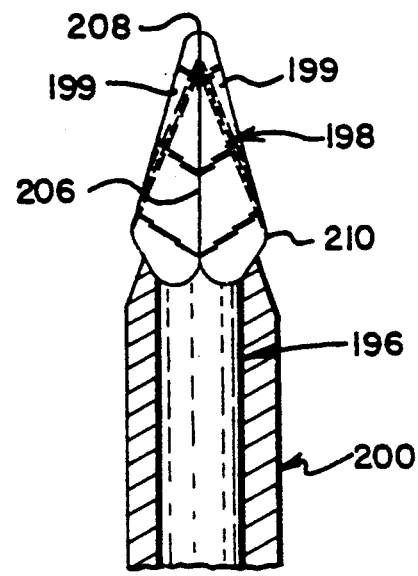
FIG. 28 is a side view of a needle and catheter.
Figure 29:
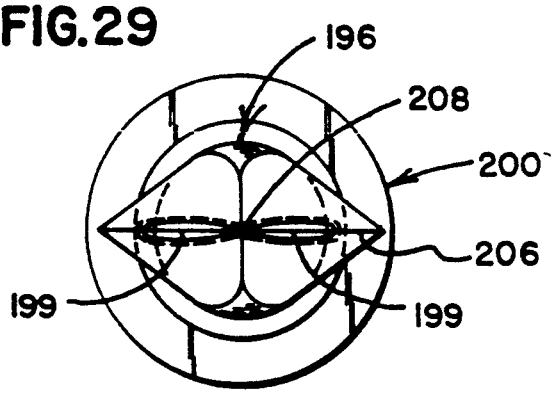
FIG. 29 is an end view of the needle and catheter of FIG. 28.
Figure 30:
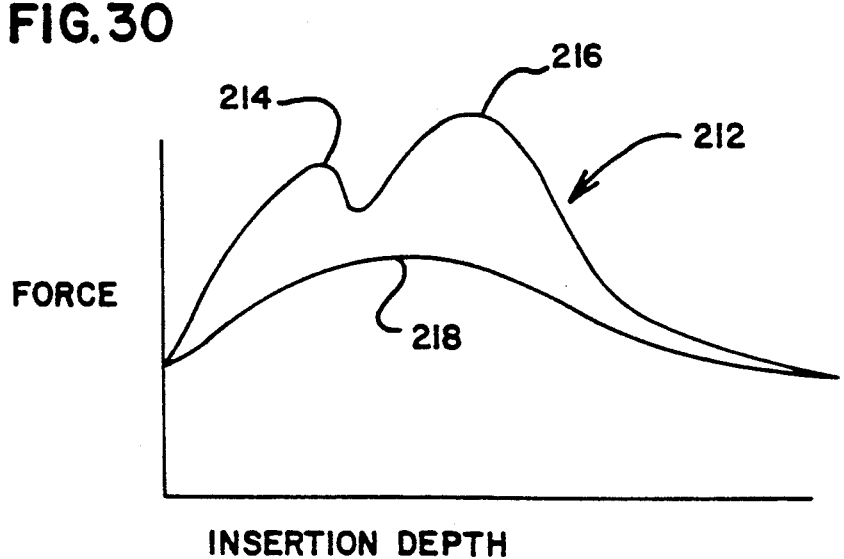
FIG. 30 is a graphic illustration of force versus distance for an insertion of two needle tips in accordance with the present invention.

Introducer 22 is a needle with a solid shaft 96 with a tip 98. Shaft 96 is preferably uniformly cylindrical. In particular, the portion of shaft 96 which extends beyond guard 32 when device 20 is in the second position, called the distal end portion, has a uniform cross-sectional shape. Tip 98 is preferably multi-faceted. In this regard, a preferred needle tip 198 for a shaft 196 with a catheter 200 received thereon is shown in FIGS. 28 and 29. Tip 198 is coined or reshaped by forcing metal to extrude out when a pair of mating dies 202 and 204 as shown in FIG. 27 come together. Tip 198 is reshaped from a conical or other shape to a multi-faceted shape as shown in FIG. 28. Tip 198 is elongated in one dimension and has knife-like edges 206 extending away from the apex 208. Edges 206 are formed at the end of rather flat burr portions 199 extending out from the body of the tip. The flattened burr portions cut even better than two flat facets coming together at an edge. Some material tends to build-up in a transition region 210 between the tip and the shaft. Furthermore, the transition region may be transversely elongated or elliptical since the tip is preferably longer in one dimension than the other. It is noted that the end of catheter 200 should be formed to mate most closely with transition region 210 to reduce any increased resistance during insertion.

A force versus insertion depth graph is shown in FIG. 25 as a comparison of the relative force required for a conical tip insertion and a multi-faceted tip insertion. Curve 212 shows a force peak 214 as the conical tip is forced through the skin and another force peak 216 when the end of the catheter is forced through. Curve 218 shows only one force peak at a level substantially lower from peaks 214 and 216. The force curve due to the multi-faceted tip is relatively lower since the knife-like edges cut an opening in the skin, rather than tear.

Introducer 22 in the preferred form with a coined tip as discussed is made using a novel method as illustrated in FIGS. 24–27. A blank 201 has straight shaft 203 with a pencil point 205. Pencil point 205 is preferably conical at approximately 30° with respect to the axis of blank 201. The pencil point tip 205 is first dipped in oil. Then it is loaded into a press wherein a bottom plate 207 has a groove for receiving it. The blank is registered horizontally against a stop plate 209. As shown in FIG. 25, a press foot 211 is then lowered to clamp the middle section of introducer blank 201. As shown in FIG. 26, a press pad 213 is then lowered to form a right angle bend in the end of introducer 201 opposite tip 205. On completion of the butt bend, stop plate 209 is moved clear and dies 202 and 204 come together to reshape tip 205 in a stamping process called coining. The reshaping takes the form described hereinbefore. Thereafter, all dies, clamps, and pads release and the completed introducer is removed.

Catheter 26 is made of a material e.g. TEFLON (PTFE), which has radial and longitudinal compressive strength so that the septum does not cause it to collapse during and after insertion, yet which allows bending without kinking, at the skin after insertion. Catheter 26 advantageously has a relatively large internal diameter which just receives introducer 22. The distal end 106 of catheter 26 has a taper to match the design of tip 98 of introducer 22.

The most convenient coupler fastened to the proximal end of catheter 26 is a conventional Luer lock 28. In any case, the coupler shown in FIGS. 8 and 9 includes a central cavity 100 for receiving boss 94. A flange 102 extends outwardly from the wall of cavity 100 at the proximal end of coupler 28. Catheter 26 is fastened with a medically approved adhesive or another known fashion to the body 104 of coupler 28 so that catheter 26 opens to cavity 100.

Introducer 22 and catheter 26 have longitudinal length relative to one another so that when flange 102 is fitted against hub 24 with boss 94 received in cavity 100, tip 98 and end 106 of catheter 26 mate in a consistent design to the degree possible such as the conical design shown. When hub 24 is received and fastened in bore 64 of handle 30, introducer 22 and catheter 26 extend beyond handle 30 to about half way along the length of guard 32 when handle 30 and guard 32 are locked in the first position. In this way, when handle 30 and guard 32 are moved to the second position, introducer 22 and catheter 26 extend beyond flange 78 of guard 32 sufficiently far to accomplish an effective insertion to port 38.

Lock pin 34 includes pin 108 fastened to a plate-like handle 110. Pin 108 has dimensions which allow it to fit into openings 74 and 88 and extend through both without interfering with catheter 26 and introducer 22 which are located approximately along the axis of handle 30 and guard 32.

Figure 11:
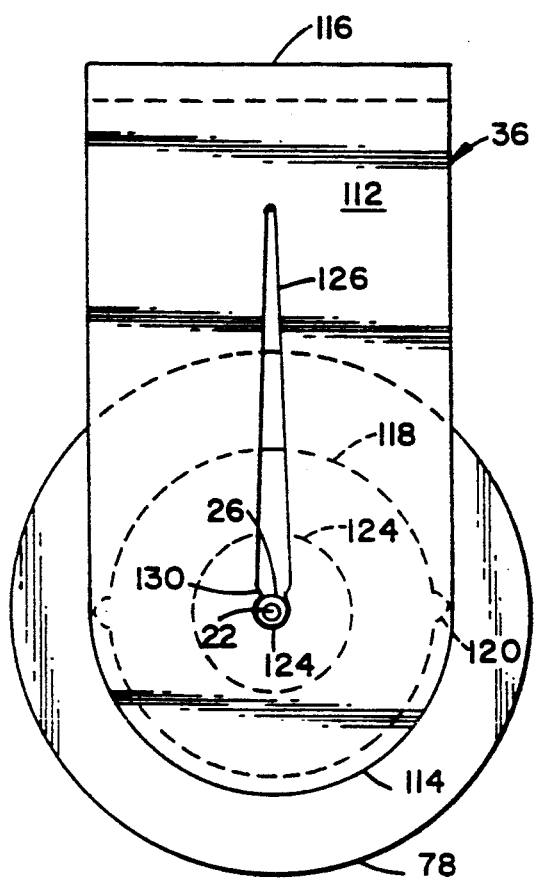
FIG. 11 is an end view of the access device taken along line 11—11 of FIG. 8.

Clamp 36 provides functions of at least partially protecting the tip of introducer 22 located within guard 32 before insertion, guiding and supporting introducer 22 and catheter 26 during insertion, and remaining on catheter 26 to provide a clamping feature for catheter 26 after insertion. Clamp 36 then has a flat member 112 and a hub 118. Flat member 112 has a semi-circular end 114 (see FIG. 1) at one end, smaller and concentric to conform to flange 78, and a handle portion which extends outwardly beyond flange 78 at the other end 116. A hub 118 is formed on flat member 112 to snugly fit into the hollow distal end of guard 32. Hub 118 includes one or more ridges 120 (see FIG. 9) along a side of hub 118. Grooves 122 are formed in the distal end of guard 32 to frictionally receive ridges 120 thereby holding clamp 36 to the end of guard 32 until moved therefrom. An opening 124 is formed along the axis of hub 118 and flares to a greater dimension in the direction of guard 32. Opening 124 has a circular dimension only slightly greater than that of catheter 26. A slot 126 (see FIG. 1) extends toward end 116 and has an ever decreasing width as it extends away from opening 124. When catheter 26 is forced into slot 126, it functions to constrict the wall of catheter 26 and eventually clamp it closed. As shown in FIG. 11, a constriction 130 separates opening 124 from slot 126. In this way, the walls of opening 130 provide a supporting function to introducer 22 and catheter 26 as they are being pressed and forced through septum 44. Constriction 130 prevents introducer 22 and catheter 26 from bowing into slot 126.

Figure 12:
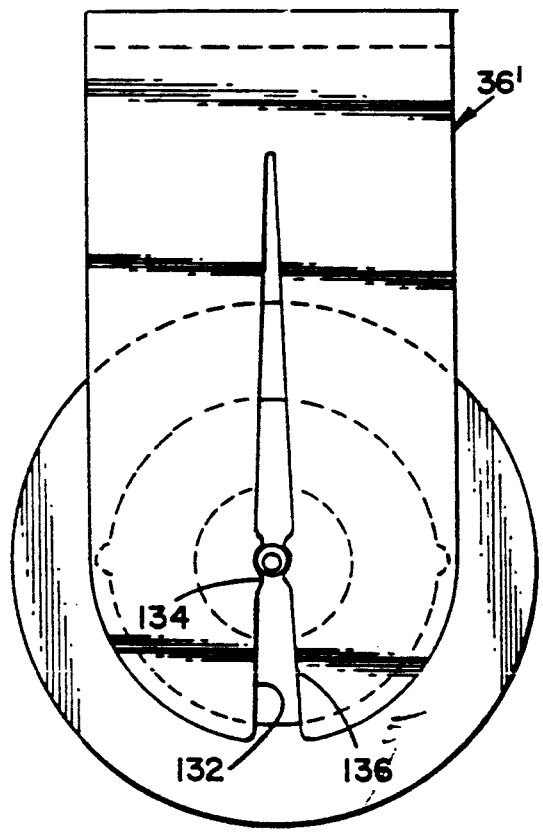
FIG. 12 is a view similar to FIG. 11 for an alternate embodiment of the catheter clamp.

In an alternate embodiment as shown in FIG. 12, equivalent elements are given equivalent numbers except they are primed. Clamp 36' is similar to clamp 36, except it includes an ever increasing slot 132 opposite from slot 126 with a second constriction 134 between opening 124 and 132. Slot 132 allows for the removal of clamp 36' from catheter 26 if it is not desired to have clamp 36' continuously attached to catheter 26. Constriction 134 has a similar size and function as constriction 130. In addition, to insure adequate support for introducer 22 and catheter 26, with this embodiment it is preferable for guard 32 to include a key (not shown) which fills slot 132.

Figure 13:
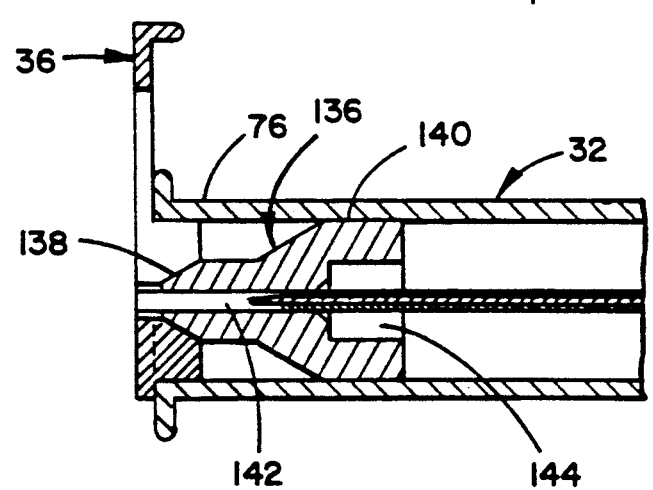
FIG. 13 is a cross-sectional view similar to FIG. 8 of a portion of the access device showing also a guide member.

Stabilizer member 136 is another mechanism for achieving support for catheter 26 and introducer 22 near the distal end of guard 32 as shown in FIG. 13. Stabilizer member 136 has a frusto-conical distal end 138 which mates with the flared end of opening 124. The proximal end portion 140 of stabilizer member 136 extends to sidewall 76 thereby providing stability and solid support. Stabilizer member 136 includes a central opening 142 having a slightly greater dimension than catheter 26 so as to provide the desired support for the central portions of introducer 22 and catheter 26. A larger cavity 144 is formed in the proximal end portion of stabilizer member 136 so that after insertion and subsequent retraction of introducer 22, stabilizer member 136 may be moved against coupler 28 so that there is a frictional fit between the wall of cavity 144 and body 104 of coupler 28. Preferably, opening 142 is several times longer than opening 124 in clamp 36 so that when desired, stabilizer member 136 provides substantially more support for shaft 22 and catheter 26 than does clamp 36.

The method of using apparatus 20 is depicted in the illustrations of FIGS. 2–7. In general, the concept of apparatus 20 is to insert a solid introducer axially surrounded by a catheter through the skin of the person or animal and the septum of the port. Thereafter, the introducer is retracted and removed from the catheter so that the catheter remains as emplaced through the skin and septum. Additional fluid mechanism can then be connected to coupler 28 and metered through coupler 28 and catheter 26 to the reservoir 46 of port 38.

Figure 5:
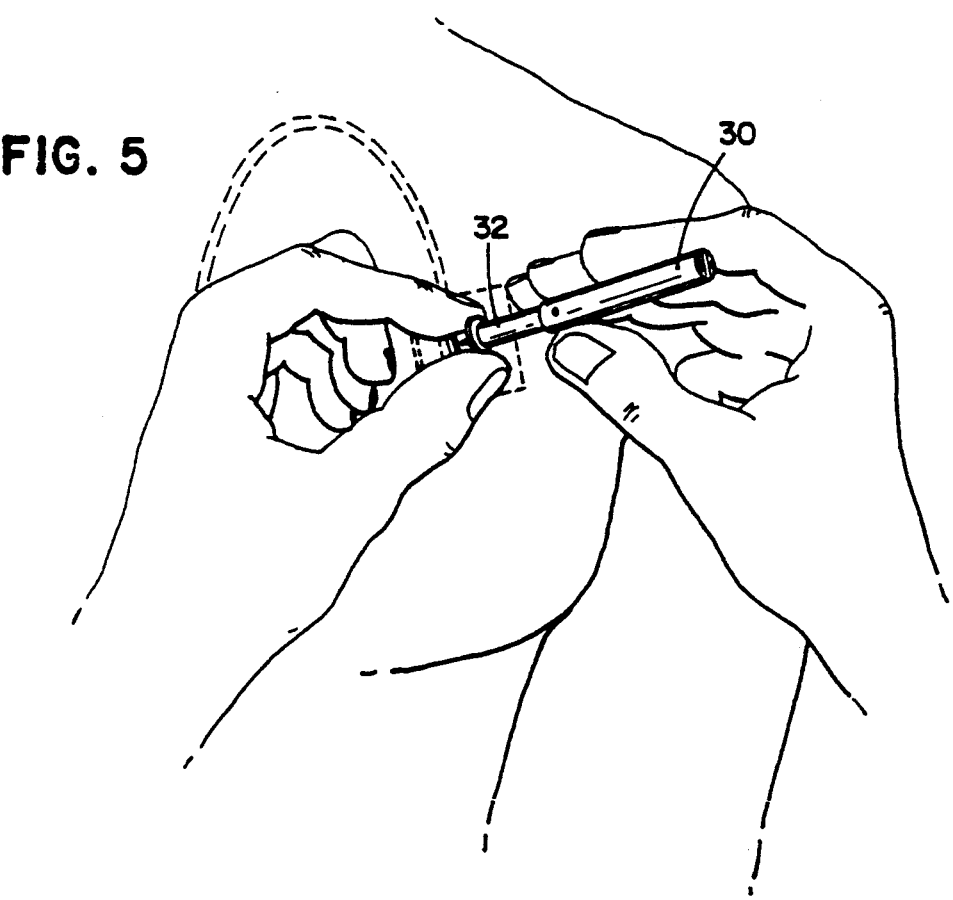
FIG. 5 is a perspective view of the guard telescoping out of the handle to protect the introducer as it is being retracted.
Figure 6:
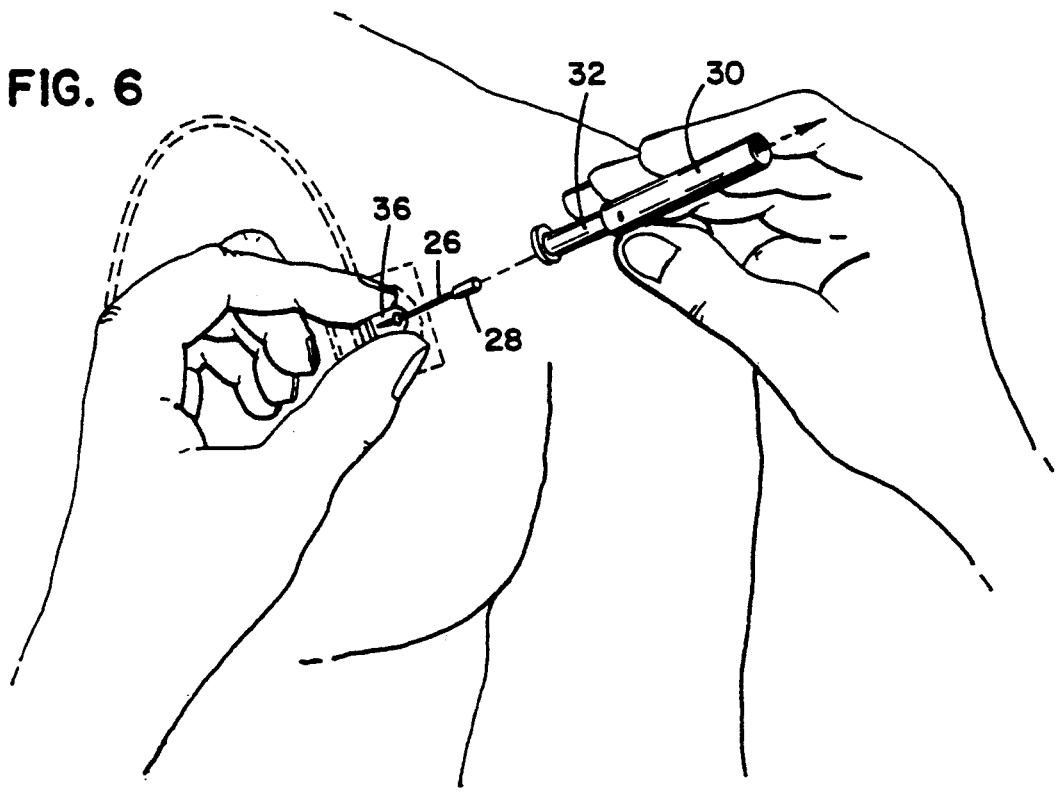
FIG. 6 is a perspective view of the covering containers being removed from the catheter with the catheter clamp remaining on the catheter.
Figure 7:
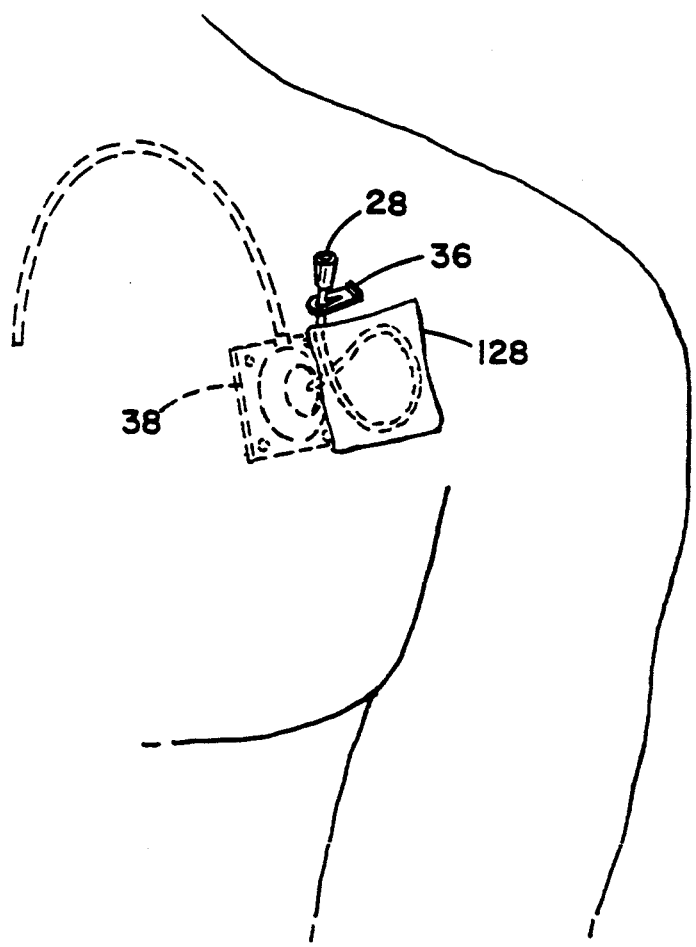
FIG. 7 is a perspective view showing the inserted catheter with respect to the implanted port.

More particularly, as shown in FIG. 2, handle 30 and guard 32 are unlocked with respect to one another by removing locking pin 34 from openings 74 and 88. Locking pin 34 may be discarded as it has no further function. As shown in FIG. 3, guard 32 is telescoped into handle 30 by holding handle 30 in one hand by holding clamp 36 or flange 78 in the other hand and pushing guard 32 into handle 30. This movement exposes the distal end portions of introducer 22 and catheter 26. Before inserting the catheter and introducer, the skin in the vicinity of port 38 is palpated to find the rim of port 38. The catheter and introducer are then held at approximately a 90° angle with respect to the skin and inserted through the skin and the septum. Apparatus 20 is forced toward the body until tip 98 reaches the bottom of reservoir 46. As shown in FIG. 5, retraction of introducer 22 back into a covering configuration by handle 30 and guard 32 is accomplished by holding guard 32 in a relatively fixed relationship with respect to the skin and pulling back on the handle with the free hand. The catheter 26 will be held by the strong frictional force developed between the catheter and the septum. That force is more than sufficient to overcome any smaller frictional force which may be developed between introducer 22 and catheter 26 and between coupler 28 at cavity 100 and boss 94. Thus, catheter 26 and coupler 28 will remain relatively stationary, while introducer 22 will be retracted from catheter 26 as handle 30 is moved away from the patient. As illustrated in FIG. 6, when handle 30 has been moved sufficiently far, arms 80 will force protrusions 82 into openings 86 to lock handle 30 and guard 32 in the third position relative to one another so that introducer 22 is longitudinally surrounded by the containers. Clamp 36 is pulled from the distal end of guard 32, and introducer 22, handle 30 and guard 32 are separated from catheter 26 and coupler 28. Clamp 36 remains on catheter 26 between coupler 28 and the skin of the patent as shown in FIG. 7. A dressing 128 may be used to hold catheter 26 to the skin of the patient thereby providing a strain relief for catheter 26 with respect to port 38.

An alternate embodiment of the access device in accordance with the present invention is shown in FIGS. 14–18 and is designated generally by the numeral 20″. Device 20″ includes an introducer 22″ with a hub 24″. The introducer fits within a catheter 26″. The hub 24″ which holds introducer 22″ is held securely at the proximal end of handle 30″. Guard 32″ telescopes into and out of handle 30″. During pre-insertion, a locking pin (not shown) similar to locking pin 34 holds the handle 30″ and guard 32″ in a fixed relationship.

Catheter 26″ includes first and second tubes 150 and 152 with a connector 154 therebetween. First tube 150 is less flexible than second tube 152. First tube 150 is preferably made from TEFLON material (PTFE) which will hold radial and compressive rigidity to the extent necessary when forcing the introducer and tube through a septum and remaining therein. Second tube 152 is preferably made from a resilient material like polyvinylchloride (PVC) of a type which can be collapsed in a clamping fashion and when released, will retain memory of its original shape. A catheter having both a semi-rigid tube and a flexible tube serves both the purpose of making insertion in the desired environment possible and also the purpose of clamping so that the catheter need not ever be open. It is desirable to clamp the catheter, for example, when removing one type of fluid and installing a second. Also, the present catheter can be made of a short length and when other fluid systems are removed, blood may be drawn if desired.

Connector 154 provides a connecting function between the less flexible tube 150 and the more flexible tube 152. Each tube has different internal and external diameters, and the connector 154 has appropriate bosses and passages for receiving each. In particular, first tube 150 is inserted and fastened within an axial passage 156 which extends the longitudinal length of connector 154. Flexible tube 152 fits over boss 158 located at the proximal end of connector 154. Connector 154 is formed to have wing members 160 which extend transversely with respect to handle 30″. Wing member 160 has sufficient thickness and sufficient length to provide sufficient structure to receive the force of handle 30″ and adequately support and pass along sufficient force to first tube 150 during insertion.

Catheter 26″ includes a Luer lock or other appropriate coupler 28″ at the proximal end of flexible tube 152. Medically approved adhesives are used to fasten coupler 28″ and connector 154 to first and second tubes 150 and 152.

Handle 30″ is cylindrical and hollow. The proximal end portion 62″ is formed to have a frustoconical bore 64″ to receive hub 24″. A plurality of ribs 162 extend from bore 64″ toward the distal end of handle 30″ to a location where the distal end 164 contact the proximal ends 166 of wing member 160 when coupler 28″ is received on the boss 94″ of hub 24″. Ribs 162 extend transversely inwardly sufficiently far so as to contact wing member 160 which extends transversely outwardly from the axis of handle 30″. Ribs 162 are spaced apart sufficiently far so that coupler 28″ can pass between them.

Guard 32″ is cylindrical and includes a stabilizer member 136″ at the distal end. Stabilizer member 136″ is removable from guard 32″ and is split so that it falls away from catheter 26″ when it is removed from guard 32″.

Handle 30″ and guard 32″ include openings for cooperation with a locking pin to hold the containers in the pre-insertion position.

With respect to the post-insertion locking mechanism, guard 32″ includes a relatively, circumferentially short flange 168 (see FIG. 18) on opposite sides of guard 32″. Handle 30″ has U-shaped channels formed along opposite sides extending from at least the distal end of wing member 160 to the distal end of handle 30″. Short flanges 168 are guided along channels 170 in the same fashion that protrusions 82 follow grooves 90 with respect to device 20. Handle 30″ includes arms 80″ cut in each outer wall of channels 170. Arms 80″ are cantilevered from the more proximal end. Near the distal end, each arm includes a ramp 172 extending inwardly and toward the distal end. A groove 174 follows ramp 172. The distal side of groove 174 is formed by a wall 176. As guard 32″ is slid from the second position as described with respect to device 20, toward the third position, flanges 168 cam arm 80″ outwardly as flanges 168 move along ramps 172. When flanges 168 are received in grooves 174, guard 32″ and handle 30″ are locked with respect to one another in the third position.

Preferably, channels 170 are oriented 90 degrees with respect to wing member 160. Such orientation is achieved by an appropriate pair of notches in coupler 28" which receive protrusions 178 extending from hub 24" (see FIG. 17).

The method of use of access device 20" is similar to device 20 and need not be further described.

Figure 19:
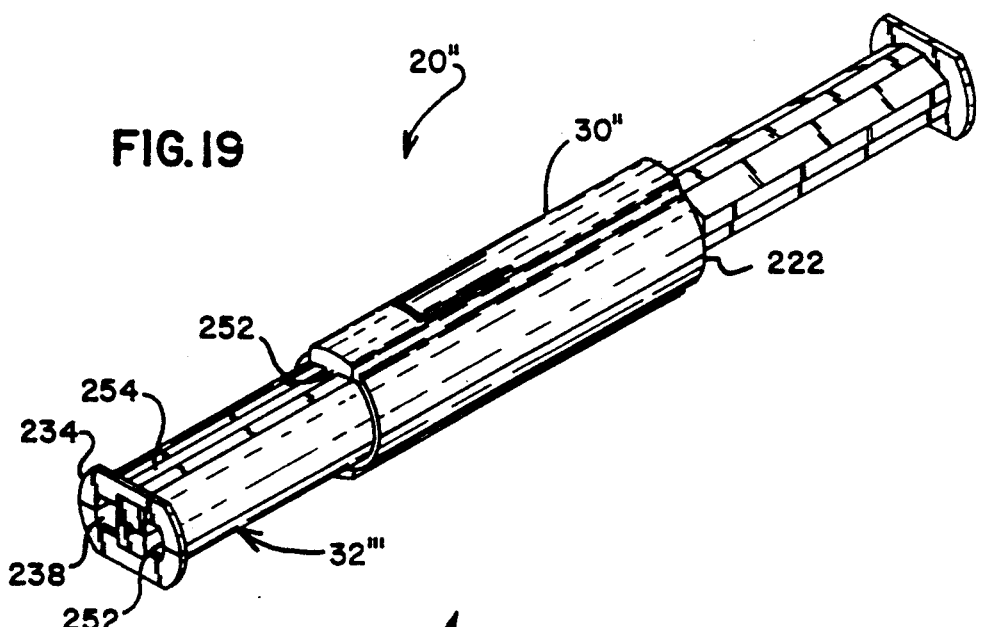
FIG. 19 is a perspective view of an alternate embodiment.
Figure 20:
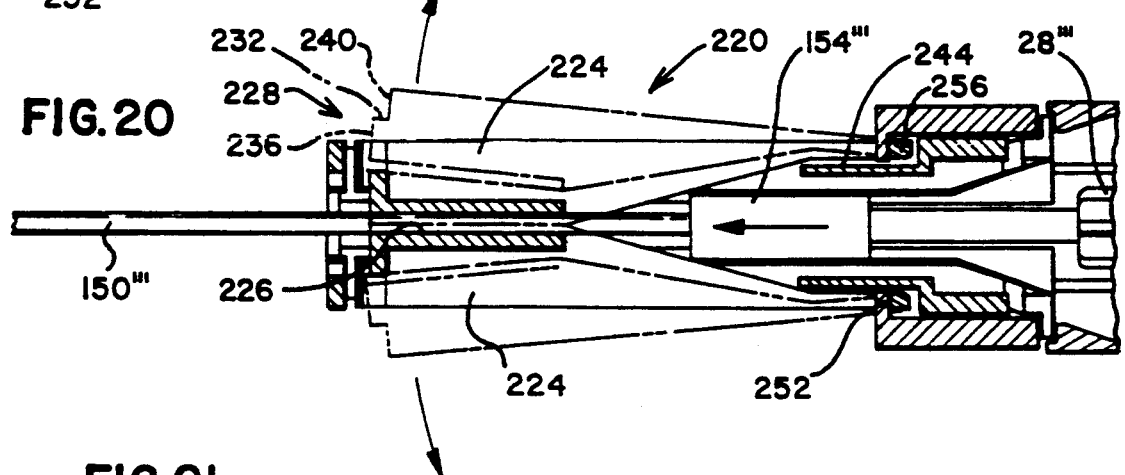
FIG. 20 is a cross-sectional view of the distal end of the embodiment of FIG. 19 showing the insertion configuration of the needle and catheter stabilizing legs in solid lines and the retraction configuration in broken lines.
Figure 21:
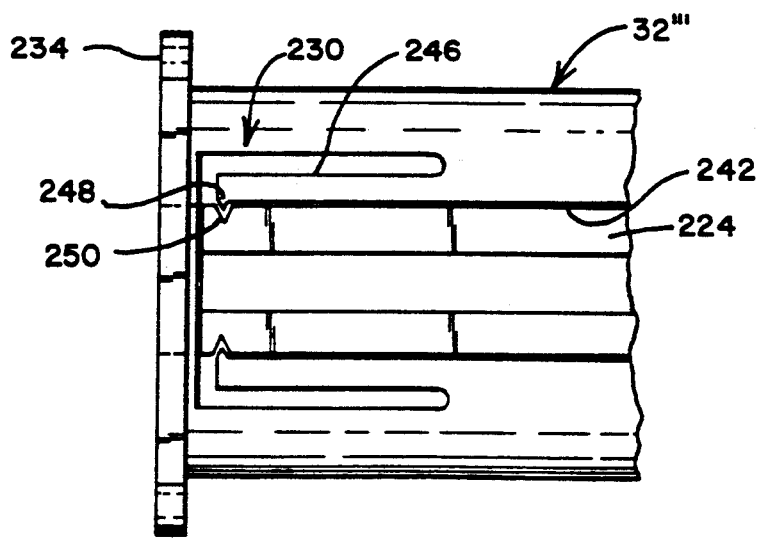
FIG. 21 is an enlarged side view of the distal end of the embodiment of FIG. 19.

A further alternate embodiment of an access device in accordance with the present invention is shown in FIGS. 19-21 and is designated by the numeral 20'". As shown in FIG. 19, device 20'" has a handle container 30'" and a guard container 32'". Although both containers are shaped somewhat differently from earlier described embodiments, except for a pre-insertion locking mechanism, all features of the earlier described embodiments are included in device 20'". The mechanism 220 for stabilizing the needle introducer and catheter at the distal end of the device differs from the earlier described mechanism and is hereafter described in detail. Another difference to note is that handle container 30'" includes a radially extending wall 222 having a surface which makes contact with the wings of the connector of the catheter so as to provide the catheter pushing function during insertion.

Stabilizing mechanism 220 includes a pair of identical arms 224. Arms 224 have mating grooves 226 which receive catheter 150'" and a needle within catheter 150'" therebetween. Grooves 226 have sufficient length to provide radial support at the end of device 20'" such that bending or kinking does not occur during insertion. Arms 224 cooperate with containers 30'" and 32'" to have first and second locking mechanisms 228 and 230 which keep arms 24 together during pre-insertion and insertion positions of device 20'". Locking mechanism 228 includes a notch 232 in the outer distal end of each arm. With arms 224 together and pushed toward flange 234 of guard container 32'", notches 232 allow the extended portion 236 of arms 224 to project into the opening 238 in flange 234, while allowing the recess portion 240 of the end of arms 224 to fit snug against the back or proximal side of flange 234. Locking mechanism 230 holds arms 224 from inadvertently sliding away from flange 234. As shown in FIG. 21, guard container 32'" has slots 242 on opposite sides extending from flange 234 to a recessed ledge 244. Guard 32'" has a cantilevered member 246 on each side of slot 242. The cantilevered member extends toward flange 234. Each cantilevered member 246 includes a small protrusion 248 extending into slot 242 and which mates with a notch 250 in arm 224.

Handle container 30'" has a protrusion 252 on opposite sides thereof at its distal end. Each arm 224 includes a slot 254 facing outwardly into which protrusion 252 fits. Slots 254 end at bridge 256. During retraction of the needle from the catheter after the catheter has been inserted so that handle container 30'" is being pulled away from guard container 32'", protuberance 252 slides and is guided in slot 254 and eventually contacts bridge 256 whereupon arms 224 are pulled so that cantilevered members 246 flex allowing protrusions 248 to come out of notches 250. As arms 224 are pulled away from flange 234, connector 154'" contacts the wedge-shaped proximal end of arms 224 and causes them to pivot about bridges 256 which are captured between recessed portions 244 of guard container 32'" and the wall and protuberance 252 of handle container 30'". It is noted that guard container 32'" has an elongated hollow interior 258 which is shaped to receive and maintain a particular orientation for connector 154'" as it moves with respect to arms 224. Arms 224 pivot outwardly through slots 242 sufficiently far to allow not only connector 154'" to pass therebetween, but also coupler 28'" thereby allowing complete separation of the catheter from the rest of device 20'".

In an alternate embodiment, now preferred, of the structure discussed in the previous paragraph, recess portions 244 are separated as appropriate from guard container 32'" to form cantilevered members 260 as shown in FIGS. 22 and 23. Cantilevered member 260 has an outwardly extending wedge portion 262 at its distal end which is inclined toward the distal end of device 20'". The proximal end 264 of wedge portion 262 is separated from a wall 266 by a distance sufficient to receive bridge 256 of an arm 224. Wall 266 is separated from the proximal connected end 268 of the recessed portion now formed as cantilevered member 260 by a distance sufficient to receive both bridge 256 and protrusion 252 of handle container 30'".

In the pre-insertion and insertion positions, bridge 256 is captured in the space between wedge portion 262 and wall 266 and actually functions as a locking mechanism so that in this embodiment locking mechanism 230 is not required. As the device is moved from an insertion position to a post insertion position, protrusion 252 contacts wedge portion 262 and forces cantilevered member 260 downwardly to allow both bridge 256 and protrusion 252 to pass over wall 266 and be captured in the space between wall 266 and proximal end 268 of cantilevered member 260. Such position is shown in FIG. 23. In this configuration, the device is prevented from being reused since there is no easy way to again pivot cantilevered member 260 downwardly so that protrusion 252 and bridge 256 can be moved out of the space between wall 266 and proximal end 268. This insures that a used insertion device must be discarded.

The method of use of device 20'" is similar to the devices described hereinbefore, although the stabilizing mechanism functions as just described. It is noted that the method of making a device in accordance with the present invention can include the novel step of coining a knife-like edge extending from the tip of a solid rod as shown in FIG. 28, before attaching the rod to a handle container. Thereafter, a catheter is slid onto the rod. As a guard container is slid into the handle container, a stabilizer mechanism is fitted about the catheter and rod combination. In some embodiments, a locking mechanism is used to hold the guard and handle containers in a pre-insertion position. Such locking mechanism is not used with respect to device 30'" since packaging holds the proper position and packaging is not removed until device 30'" is ready to be used. Thereafter, as indicated, the method of use follows the description provided hereinbefore.

Finally, a still further alternate embodiment of an access device in accordance with the present invention is shown in FIGS. 31 and 32 and is designated generally by the numeral 20''''. The only difference between access device 20'''' and devices having various features already described is that the pushing mechanism 270 has a collapsible portion 274 which allows the tip 198'''' of introducer 22'''' to be pushed into catheter 26'''' when the tip contacts and is pushed against solid surface 47 of port 38. In this regard, it is noted that during insertion the septum 44 of port 38 bows downwardly toward solid surface 47 so that, although the tip 198'''' of introducer 22'''' enters reservoir 46, the distal end of catheter 26'''' may not have travelled sufficiently into the interior of reservoir 46. Consequently, it is advantageous to have a mechanism which allows introducer 22'''' to retract and allow catheter 26'''' to be inserted nearer contacts solid surface 47 as shown in FIG. 32. Then, when introducer 22'''' is retracted further and device 20'''' is separated from catheter 26'''' so that downward pressure is relieved from septum 44, the septum will return to its original position and therewith move the end of catheter 26'''' away from solid surface 47 to leave it well into reservoir 46, but away from various walls of the reservoir.

The pushing mechanism 270 includes a hub 24'''' to which the proximal end of introducer 22'''' is fastened. Device 20'''' has a solid proximal end 272. The space between hub 24'''' and end 272 is filled with a yieldable material 274 which has properties allowing it to be rigid at force levels sufficient to insert introducer 22'''' and catheter 26'''' through a patient's skin and the septum 44 of a port, but which will yield and collapse when more force is applied at the time tip 198'''' contacts solid surface 47. Yieldable material 274 must collapse sufficiently to allow tip 198'''' to be pushed into, or at least pushed a significant distance, into reservoir 46.

Although numerous advantages of the present invention have been mentioned hereinbefore, a further advantage arises on a consideration of device 20'''' and the most popular prior art device as shown in FIGS. 33-36. The most common present method of accessing a port is by inserting a needle 276. Needle 276 is hollow and so as to avoid coring a septum 44 too badly, the tip is either formed as an inclined wedge or in a boat-like configuration. In either case, the opening 278 at the tip extends along an elevational distance with respect to solid surface 47. Often, because of the bowing of septum 44 during insertion, opening 278 remains partially obstructed by a portion of septum 44 as shown in FIG. 34. When pressure is relieved on septum 44 after insertion of needle 276 as shown in FIGS. 35 and 36, the tip of the needle retracts somewhat from solid surface 47, but opening 278 remains partially obstructed. Since the passage through needle 276 is small in the first place in order to avoid a significant coring problem, the additional obstruction as described can lead to situations where it is difficult to flow a sufficient quantity of fluid through the apparatus in its intended fashion. Device 20'''', in particular, nicely overcomes the indicated problem.

Thus, preferred and alternate embodiments and methods of making and using the invention have been described in detail and advantages of structure and function have been set forth. It is understood, however, that equivalents are possible. Therefore, it is further understood that changes made in the structure and the use of the disclosed invention, especially in matters of shape size and arrangement, to the full extent extended by the general meaning of the terms of which the appended claims are expressed, are intended to be within the principle of the present invention.

What is claimed is:

1. A transcutaneous infusion apparatus, comprising:
   an implantable infusate injection port including a housing forming a reservoir with a self-sealing septum on an access side and a solid surface on a side opposite, said port having an outlet tube, said port being adapted for implantation in a human or animal body with the septum located under the skin and the outlet tube leading to an infusion site in the body;
   a needle having a tip and a longitudinal shaft;
   catheter means for accessing the reservoir of said port, said catheter means fitting about a portion of said shaft of said needle while allowing said tip to be exposed; and
   means for holding said needle and said catheter means in order to insert said needle and said catheter means through said septum, said holding means including means for pushing said needle and said catheter means during insertion until said needle contacts said solid surface of said port, said pushing means including means for yielding with respect to said needle to allow said catheter means to more closely approach said solid surface, said yielding means comprising a yieldable material which is generally rigid at force levels sufficient to introduce said needle and said catheter means through said septum but which will yield and collapse when greater force is applied thereto, said needle and said holding means being separable from said inserted catheter means.

2. Apparatus in accordance with claim 1 wherein said catheter means includes a catheter having proximal and distal ends and a wall intermediate said catheter proximal and distal ends with a surface transverse with respect to said catheter and wherein said pushing means also includes means for contacting said transverse surface.

3. Apparatus in accordance with claim 1 wherein said holding means has a distal end and a proximal end opposite the distal end, said holding means including a pair of arms, said arms having mating grooves therein to receive and support said catheter means and said needle.

4. Apparatus in accordance with claim 3 wherein said holding means has first, second, and third positions, said first position longitudinally covering said catheter means and said needle, said second position exposing portions of said catheter means and said needle for insertion, said third position longitudinally covering said needle, said apparatus further including first and second means for locking said arms relative to said holding means when said holding means is in said first and second positions.

5. Apparatus in accordance with claim 4 including means for unlocking said arms relative to said holding means as said holding means is moved from said second position to said third position.

6. Apparatus in accordance with claim 5 wherein said catheter means includes first and second tubes with a connector therebetween and a coupler on an end of said second tube opposite said connector, said arms when unlocked having positions separable from one another to allow said connector and said coupler to move therebetween when said catheter means is separated from said holding means.

7. Apparatus in accordance with claim 1 wherein said holding means has first, second, and third positions, said first position longitudinally covering said catheter means and said needle, said second position exposing portions of said catheter means and said needle for insertion, said third position longitudinally covering said needle, said apparatus further including means for preventing movement of said holding means from said third position.

8. A catheter introducer assembly comprising:
   a solid needle having a proximal end and a distal tip;

a catheter having a proximal end and a distal tip, the catheter being slidably received over the needle;

a first housing member, the proximal end of the needle being housed by and affixed to the first housing member;

a second housing member receivable over the distal tips of the needle and catheter, the first and second housing members being telescopably slidable between a first extended position whereat the distal tips of the needle and the catheter are enclosed within the second housing member and a second collapsed position whereat the distal tips of the needle and the catheter are exposed, the first and second housing members having a combined length which is greater in the extended position than in the collapsed position.

9. The catheter introducer assembly of claim 8 further comprising rigid means affixed to the catheter for receiving a pushing force, the first housing member including means internally thereof for applying a pushing force to the rigid means of the catheter as the housing members are telescoped from the first position to the second position.

10. The catheter introducer assembly of claim 9, the rigid means of the catheter including wing members extending transversely relative to the catheter.

11. The catheter introducer assembly of claim 9, the rigid means of the catheter including a connector at the proximal end of the catheter.

12. The catheter introducer assembly of claim 8 wherein the catheter includes a connector at the proximal end, the assembly further comprising:

guide means releasably attached to the second housing member for guiding the needle and catheter out of the second housing member as the second housing member telescopes from the first to the second position.

13. The catheter introducer assembly of claim 8, the guide means normally defining an aperture smaller than the connector, the assembly further comprising means for enlarging the aperture whereby to allow the catheter connector to pass therethrough.

14. The catheter introducer assembly of claim 8 further comprising:

yieldable means for affixing the needle to the first housing member.

15. The catheter introducer assembly of claim 8, the catheter comprising a first tube of less flexible material and a second tube of more flexible material, said first and second tubes joined by a connector member and said first tube including said catheter distal tip and said second tube including said catheter proximal end.

16. The catheter introducer assembly of claim 15, the first tube of less flexible material extending from the connector member to the distal tip of the catheter, and the second tube of more flexible material extending from the connector member to the proximal end of the catheter.

17. The catheter introducer assembly of claim 15, the connector member including wing members extending transversely of the first and second tubes.

18. The catheter introducer assembly of claim 17, the first housing member including a handle portion and an internal shoulder at the distal end of the handle portion.

19. The catheter introducer assembly of claim 18, the internal shoulder abutting the wing members for applying a pushing force thereagainst as the housing members are telescoped from the first position to the second position.

20. The catheter introducer assembly of claim 8, the needle having a knife-like edge extending away from the distal tip.

21. The catheter introducer assembly of claim 20, the knife-like edge of the needle tip including burr portions.

22. The catheter introducer assembly of claim 8 wherein said second housing member includes stabilizing means for stabilizing the catheter and needle prior to and during insertion into a patient.

23. The catheter introducer assembly of claim 22, the stabilizing means being separable from the housing members and having a first orientation defining an aperture smaller than the connector member to retain the catheter at least partially within the first and second housing members, and a second orientation defining an aperture of sufficient size to permit removal of the catheter from the first and second housing members.

24. The catheter introducer assembly of claim 23, the stabilizing means comprising at least one arm having a groove for receiving the catheter and needle, the groove having sufficient length to provide radial support for the catheter and needle to prevent bending or kinking thereof during insertion in a patient, said at least one arm pivotally received in a respective longitudinal slot in the second housing member.

25. The catheter introducer assembly of claim 24 further comprising means for causing said at least one arm to pivot outwardly of the second housing member.

26. A catheter introducer assembly comprising:

a solid needle having a proximal end and a distal tip;

a catheter comprising a first tube of less flexible material including a catheter distal tip and a second tube of more flexible material including a catheter proximal end, said first and second tubes joined by a connector member, the catheter being slidably received over the needle;

a first housing member, the proximal end of the needle being housed by the first housing member;

a second housing member receivable over the distal tips of the needle and catheter and including stabilizing means for stabilizing the catheter and needle prior to and during insertion into a patient, the first and second housing members being telescopably slidable between a first extended position whereat the distal tips of the needle and catheter are enclosed within the second housing member and a second collapsed position whereat the distal tips of the needle and catheter are exposed.

27. The catheter introducer assembly of claim 26, the stabilizing means comprising a pair of arms having mating grooves for receiving the catheter and needle therebetween, the mating grooves having sufficient length to provide radial support for the catheter and needle to prevent bending or kinking thereof during insertion in a patient, each of the arms pivotally received in a respective longitudinal slot in the second housing member.

28. The catheter introducer assembly of claim 27 further comprising means for causing said arms to pivot outwardly of the second housing member.

29. The catheter introducer assembly of claim 27, the arms and the first housing member having cooperating radially extending flanges and corresponding longitudinal slots in which the flanges are slidably received as the housing members are telescoped from the first position to the second position.

30. The catheter introducer assembly of claim 29, the first housing member having a pair of channels formed therein and a pair of cantilever arms having a free end, each cantilever arm having inwardly extending ramp means at the free end thereof.

31. The catheter introducer assembly of claim 30, the second housing member having a pair of radially outwardly extending flanges slidably receivable in the channels in the first housing member, the flanges riding in the channels, biasing the cantilever arms outwardly as they ride on the ramp means, and positively locking the first and second housing members in a third extended position whereat the distal tip of the needle is enclosed within the second housing member.

32. A catheter introducer assembly comprising:
 a solid needle having a proximal end and a distal tip;
 a catheter having a proximal end and a distal tip, the catheter being slidably received over the needle;
 a first sleeve member having a distal end portion; and
 a second sleeve member having a distal end and a proximal end, the proximal end adapted to be telescopically slidable with respect to the distal end portion of the first sleeve member, the sleeve members having a first extended position with respect to one another wherein the sleeve members surround the needle and the catheter, the sleeve members having a collapsed position with respect to one another wherein the needle and the catheter extend outwardly from the distal end of the second sleeve, and the sleeves having a second extended position with respect to one another wherein the sleeves surround the needle after retraction of the needle from the catheter after introduction of the catheter, the first and second sleeve members having a combined length which is greater in the extended position than in the collapsed position.

33. The catheter introducer assembly of claim 32 further comprising locking means for locking the sleeves in the second extended position.

* * * * *